United States Patent
Duncan

(10) Patent No.: US 6,663,679 B1
(45) Date of Patent: Dec. 16, 2003

(54) HIGH INTENSITY, NON-REVERSING HUMIDITY INDICATOR

(76) Inventor: William P. Duncan, 31 Berkley Rd., Hopatcong, NJ (US) 07843

( * ) Notice: Subject to any disclaimer, the term of this patent is extended or adjusted under 35 U.S.C. 154(b) by 0 days.

(21) Appl. No.: 10/154,551

(22) Filed: May 23, 2002

(51) Int. Cl.[7] .................. G01N 09/00; G01N 005/02; G01D 21/00; G01D 53/02
(52) U.S. Cl. .................. 23/335.01; 73/73; 73/29.01; 116/206; 96/117.5
(58) Field of Search .................. 73/73, 76, 29.01, 73/29.02, 335.01, 29.04, 29.05; 116/206; 206/524.5; 96/117.5, 118

(56) References Cited

U.S. PATENT DOCUMENTS

| | | | | |
|---|---|---|---|---|
| 1,933,803 A | * | 11/1933 | Hickman | 73/335.01 |
| 2,214,354 A | | 9/1940 | Snelling | |
| 2,249,867 A | | 7/1941 | Snelling | |
| 2,504,299 A | * | 4/1950 | Cartwright | 116/206 |
| 2,534,279 A | * | 12/1950 | LibertHson | 73/73 |
| 2,687,041 A | * | 8/1954 | Anderegg | 73/29.02 |
| 3,675,654 A | | 7/1972 | Baker et al. | |
| 4,063,452 A | * | 12/1977 | Bradshaw | 73/73 |
| 4,126,907 A | * | 11/1978 | Fish | 441/8 |
| 4,454,831 A | * | 6/1984 | Gallo | 73/73 |
| 4,793,180 A | * | 12/1988 | Stewart et al. | 73/29.02 |
| 5,224,373 A | | 7/1993 | Williams et al. | |
| 5,780,721 A | | 7/1998 | Levens | |
| 6,131,443 A | | 10/2000 | Duncan | |

* cited by examiner

Primary Examiner—Edward Lefkowitz
Assistant Examiner—Michael Cygan
(74) Attorney, Agent, or Firm—Myers & Kaplan, LLC; Joel D. Myers; Thomas R. Williamson, III

(57) ABSTRACT

The invention is a device for monitoring humidity, comprising a first layer, which is a visual indicator, a second layer covering and obscuring the first layer, with the second layer comprising a deliquescent material. The deliquescent material picks up moisture and dissolves itself in the moisture, becoming transparent and exposing the first layer. Also included is a viewing means, such as a sight glass, disposed on the opposite side of the second layer from the first layer. The components of the device are mounted or placed in an enclosure that allows entrance of moisture. The activation humidity level may be selected by choosing the appropriate deliquescent material. The device may be in the form of a component of a moisture-containing system and used to detect the moisture should it leave its containment. It may also be in the form of a stand-alone device, such as a capsule, used to monitor exposure to humidity. Additionally, the device may be formed with indication of exposure to different levels of humidity.

24 Claims, 3 Drawing Sheets

SECTION A-A

HIGH INTENSITY, NON-REVERSING HUMIDITY INDICATOR

CROSS-REFERENCES TO RELATED APPLICATIONS

None

FEDERALLY SPONSORED RESEARCH

Not Applicable

SEQUENCE LISTING, TABLE OR COMPUTER PROGRAM

Not Applicable

FIELD OF THE INVENTION

The present invention is directed to the field of humidity monitoring devices.

BACKGROUND OF THE INVENTION

Humidity, or the level of moisture in an environment, is a critical concern for many applications. There are many systems and materials that can be damaged by the presence of water. Accordingly, it is important to have a method to determine the presence of moisture and even small quantities of water vapor at varying levels of humidity. Additionally, many piping systems contain fluids, principally composed of water, that have a deleterious effect on the piping system itself or on other components or materials external to such a system.

Very often, in a fluid containing system, the corrosive fluid in the system is water. Even in small quantities, due to its formation as a vapor, water can lead to corrosive effects. Water presents a great threat to most forms of carbon steel and some other metal surfaces by increasing surface corrosion. Moisture can negatively affect various chemical, mechanical, and electronic processes and components, as well as the operation of some forms of equipment, if allowed to reach sufficient levels. Even low moisture levels can produce substantial damage. In worst-case examples, where there is a high humidity condition, over a sufficiently long duration, valuable product, processes, and equipment can be destroyed, or rendered useless.

Water is a component of a corroding system and will have a continual action on materials meant to contain it. At other times, ambient moisture needs to be prevented from reaching into a sensitive area.

The present invention provides a method of indicating, as part of a monitoring system, that water has escaped from its containment system or that water has entered a moisture sensitive area.

Monitoring the humidity level in such environments therefore becomes of great concern to both manufacturers and users of such humidity sensitive products and equipment. As a result, various methods of indicating humidity exist, both electronic and chemical.

In developing a humidity sensor, it is important that such a sensor be flexible in its application, error-free (such as avoiding false negative responses), persistent, unequivocal, simple in design and inexpensive to manufacture.

In use to detect the entry of moisture, the present invention may be in the form of a self-contained unit that can be placed in view inside a sensitive area. If it is not possible to have the unit in view, it may need to be incorporated within the walls containing the sensitive components. In such a case, a viewing window would be part of the detection unit. In piping systems, the present indicator invention would typically be part of a fitting mounted into the walls of the pipe.

U.S. Pat. No. 6,131,433 to the author of the present invention (Duncan) describes a corrosion monitoring device and more particularly to a self contained, disposable corrosion monitor for a fluid containing system, which indicates a breakthrough of the integrity of the wall of the system due to the corrosive action of a fluid in the fluid containing system. More particularly, the present invention may be incorporated to provide the indication that water has broken through, when used in a system where the fluid contains water.

Failures of metal pipes, tanks and other fluid enclosures due to the deterioration of their inner wall surfaces are all too common occurrences; currently causing over 10 billion dollars annually in replacement costs alone. While some corrosion induced metal failures may create a great and unexpected financial loss due to replacement cost, down time and water damage, more severe failures of high temperature and high pressure pipes and vessels may result in explosion, extensive physical damage, severe injury and human casualty. Effective corrosion monitoring is therefore greatly desired from such a production, health, environmental, process reliability, economic and liability viewpoint.

Corrosion of metal surfaces is a continuous and generally non-stoppable electrochemical process, which is well known and documented. Given sufficient time, metal failures are inevitable where fluids and metal meet and interact, and where at best, the negative physical effects of corrosion can only be minimized, not eliminated.

Due to the complex interaction of chemical, electrical and mechanical influences which determine the degree of activity of a corrosion environment, and the fact that such corrosion activity often widely varies at different locations within the same fluid environment, there is the need to monitor as many individual locations in a given piping system, tank, pressure vessel or reactor vessel as possible. The inability to monitor the corrosion activity at multiple locations within a piping system is frequently a cause of failure, since a single monitoring point, not representative of the corrosion in the entire piping system, may produce an erroneous prediction of service life and service failure.

Chemical and electrical corrosion inhibitors and other substances exist to help reduce corrosion and are often relied upon exclusively to safeguard piping and other metal components. The use of such corrosion inhibitors does not preclude the need for corrosion monitoring, however, since actual results of anti-corrosion agents vary widely, thereby making it necessary to regularly verify their efficiency and proper application.

A wide variety of corrosion monitors and procedures exist in the literature and in current use with the purpose of measuring the corrosive nature of a fluid or fluid stream against a specific metal surface. These devices are described in U.S. Pat. No. 6,131,433, incorporated herein by reference. Many monitoring devices, therefore, find limited actual field use, provide unsatisfactory corrosion monitoring coverage due to the limited number of sensors or probes installed and provide little benefit to all but the most critical of applications.

Ultrasonic testing is well recognized for providing extremely accurate remaining wall thickness measurements for any metal structure, but typically serves as a survey or an instantaneous measuring tool rather than a long term monitoring device. It has a disadvantage of being a temporary measurement instrument, is expensive, and requires an experienced operator and careful analysis and manipulation of the resulting data, as well as periodic access to the exact same area of the pipe surface for reevaluation.

DESCRIPTION OF RELATED ART

Current humidity indicators work on the basis of some chemical change occurring within a viewable material to produce a color change within that same material. Materials commonly used are based around some form of silica gel or clay or cobalt chloride. Some materials exist just as indicators of moisture, while others provide a desiccating service and also change color only after their ability to absorb moisture has been exceeded, and moisture level increases. Prior art humidity indicators vary depending upon the physical shape and differentiation in indicating ability, such as providing indication in 10% or 20% increments, although they all operate on a basic color change within a chemical compound given a certain humidity level.

The disadvantage of such indicators is that they produce a very faint color change typically varying from a light blue when new and completely dry to a faint pink or lavender when they absorb moisture. Some products offer a mildly stronger color change, or different beginning and final colors. Because the colors are faint and the change is minimal, it would not be immediately noticeable in an industrial environment without some form of prompting to view it closely. It would be unlikely to see such a color change from more than 10 feet away.

A further disadvantage of such products is that, if encountering an actual water condition and not simply a high degree of humidity, they will typically dissolve their color into the solution, or solubilize their indicator, and soon lose all potential to produce any warning. This is especially true for dye indicators that activate or react with moisture to produce their indication initially.

Therefore, if the color change were not seen within a certain period of time, it might wash out to provide no indication whatsoever and actually produce a false negative and allow a potentially dangerous condition to go unnoticed. Various applications exist where a high humidity level may precede the entry of water or a flow of water into an area, and therefore the ability of an indicator to retain its color becomes a critical feature.

U.S. Pat. No. 2,249,867 to Snelling uses a deliquescent chemical to attract water into itself so that the water can then produce a chemical color reaction within a second material adjacent to it, with the second material producing the actual color change. The colored material is described as a water-soluble dye which is activated to bring a color change after contact with water produced from the deliquescent material. That colored mixture of dye and moisture produced by the deliquescent material is then carried through a porous membrane, which previously obscured view of the chemical dye, thus producing a visual indication. Varying the deliquescent compounds used determines the point at which the deliquescent chemical begins absorbing moisture, thus producing an indication at different humidity levels.

This device, described in U.S. Pat. No. 2,249,867 to Snelling, operates on the principle of a chemical color change, does not produce a high intensity color indication, and does not employ a fixed and non-reversing color indicator. Since water contact with the dye indicator initiates the indicating reaction and allows the color to seep through the porous medium, submersion in water would dissolve and disperse the dye and therefore render the indicator useless. U.S. Pat. No. 2,214,354 to Snelling is an earlier form of the above patent.

U.S. Pat. No. 3,675,654 to Baker et al. also uses a water-soluble dye as the indicator. It is intended as a moisture indicator for diapers or other personal hygiene items to signal the need for changing. When moisture reacts with the dye, it produces a color change which then transmits through another layer of cloth or material to signal a wetness condition at the outside of the item. This invention lacks high visibility indication and may wash out in an excess of liquid.

U.S. Pat. No. 5,224,373 to Williams et al. is a humidity sensor requiring three layers of material and is based upon a chemically-treated material that changes color in response to various humidity levels present. The indicating layer undergoes a chemical change in response to moisture that has passed through a water permeable layer. Various compositions of the materials provide indication at different humidity levels.

This device does not provide a high intensity indication and is intended for providing a flexible indicator suitable for packaging of materials. As the chemical cobalt chloride is used, an excess of water would dissolve out the cobalt chloride, causing the indicator to lose its color indication and it would be rendered useless in such potential applications.

U.S. Pat. No. 5,780,721 to Levens describes a device that is intended for the detection of chemical leaks at pipeline connections, flanges, and welds, which exists as a ring clamped or fastened around a pipe joint. This patent uses foam as its principal component, which foam is selected to dissolve in response to the presence of specific organic chemicals existing within the pipeline and leaking at adjoint or seam. After the foam dissolves away or becomes transparent, the foam reveals a pre-existing visual indicator, thus producing a warning of a chemical leak.

The method of operation of the foam is that it is applied externally, particularly to detect leakage of organic compounds. It is not self-contained and can be dissolved or broken away by other external factors unrelated to any leak. It cannot attract the organic compound and requires actual contact by the organic compound, which must migrate to it.

As described, the prior art fails to disclose a device or method suitable for monitoring humidity, that is highly visible, of high intensity, non-reversible, persistent and not susceptible to false negative responses.

Objects and Advantages

The present invention is a simple means for producing a highly visible, high intensity, warning indication when a certain degree of humidity exists in an area. The indication is non-reversible, cannot be lost or washed away if submerged in a liquid environment, and can accommodate a change from most colors to any other known color.

This humidity indicator may be used as a component of a corrosion monitor, such as that described in U.S. Pat. No. 6,131,433 to the author of the present invention (Duncan), which is incorporated herein by reference.

It is an object of the present invention to provide a brilliant visual indication not dependent upon a chemical color change, in which the color change can be to any color, tone or intensity desired. The color change of the present invention is readily discernible from distances of at least 40 feet away.

It is an object of the present invention to provide a humidity monitor using an indicator made from paint, epoxy, heat-bonded high temperature vinyl or any other material of color.

It is a further object of the present invention that it can be fabricated by simple means from safe, abundant materials.

It is still a further object that the color change of the present invention will not wash out or dissolve due to saturation in the liquid environment, and will remain to provide indication of a problem condition without the fear that noticeability of the indication will be lost if not immediately observed.

It is also an object of the present invention that it is simple in design, low in cost, easy to manufacture, and is easily adapted to various physical forms.

It is still another object of the present invention to provide a humidity monitor that can be used in any location and thus, along with its low cost, it will provide a benefit by allowing the monitoring of a greater number of areas of concern.

Still a further object of the present invention is that it cannot produce a false negative indication.

An object of the present invention is to provide an indication or signal, as part of a corrosion monitoring system, to owners and operators of any pipe, tank, pressure vessel, reaction vessel or other water containment or transmission system that a breakthrough of the containment surface has occurred.

Still a further object of the present invention is its use as a component of a disposable, self contained, stand alone device not requiring any further evaluation, energy, information processing, handling, maintenance or testing in order to produce an indication of the presence of humidity.

Still an additional object of the present invention is to provide an indicator for a corrosion monitor that can be tailored to meet any varying monitoring needs due to the various types of piping and material carrying systems operating under even more varying environmental conditions.

By reviewing and considering the drawings and descriptions further objects and advantages of the instant invention will be apparent.

BRIEF SUMMARY OF THE INVENTION

The present invention is a device for monitoring humidity, comprising a first layer comprising a visual indicator, a second layer covering and obscuring said first layer, said second layer comprising a deliquescent material, wherein, as said deliquescent material picks up moisture and dissolves itself in said moisture, it becomes transparent exposing said first layer, a viewing means disposed on the opposite side of said second layer from the first layer, and an enclosure with an entrance for moisture containing the said first and second layers and the viewing means.

REFERENCE NUMERALS IN DRAWINGS

Figure 1A:
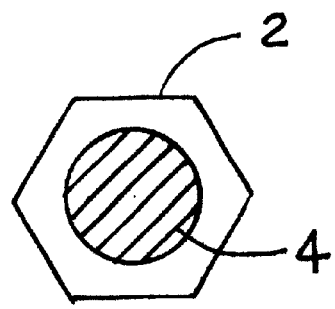
FIG. 1A depicts a top view of the humidity indicator, showing opaque deliquescent material intact.

2 Enclosure
4 Opaque deliquescent material
6 Color indicator
8 Viewing window
12 Deliquescent material layer
14 Color indicator layer
16 Spring
18 Spring stop
20 Permeable surface section

DETAILED DESCRIPTION OF THE INVENTION

The present invention produces a visual indication of humidity based upon a mechanical action initiated by the transformation of a chemical component from solid to liquid. This transformation from solid to liquid only takes place in an environment containing some degree of humidity. In effect, the chemical change in the device initiates a mechanical indication of a humidity presence.

The device consists of a clear window or viewing port, behind which rests a deliquescent chemical of various possible chemical origins and combinations, and in various possible forms, shapes, or thickness. This deliquescent material, in its dry or anhydrous form, exists as an opaque solid, and therefore prevents the viewing or observation of any material behind it, namely, material that is placed on the opposite side from the viewing location. One key function of this deliquescent chemical, as part of the present invention, is to obscure, or block the view of, a second indicating component behind it. Another key function is the deliquescence, specifically described as the change that a powdery substance goes through in that it will dissolve in the water it absorbs from the atmosphere, unless it is kept enclosed and away from a humid atmosphere. By this means, the chemical that is obscuring the view of the indicator will dissolve in the humid environment.

Unlike a standard desiccant material, such as silica clay or gel, which also absorbs moisture but holds or captures that moisture into its own fixed physical form, a deliquescent material attracts moisture and is dissolved or liquefied by the moisture it absorbs. If it absorbs sufficient moisture, the deliquescent chemical completely dissolves into a droplet or other volume of clear, colorless and transparent liquid.

A suitable deliquescent material, in one embodiment of the present invention, is lithium chloride, although any number of deliquescent chemicals or compounds are applicable and can be used. Such deliquescent chemicals are often termed hygroscopic or hydrophilic due to their affinity for moisture in the atmosphere, which they capture and then dissolve or liquefy themselves in that captured water. Some examples of other deliquescent chemicals, although not an inventory of all possible deliquescent or hygroscopic chemicals or chemical compounds suitable for use, are: Halides, hydroxides, carbonates and nitrates of alkali metals, alkaline earths, and transition metals, particularly lithium chloride, sodium hydroxide, potassium fluoride, potassium carbonate, potassium nitrate, magnesium chloride, stannous chloride, strontium chloride, aluminum chloride, calcium chloride, zinc chloride, calcium nitrate, and sodium nitrate. Additionally, ammonium chloride and ammonium nitrate are suitable deliquescent compounds.

Certain deliquescent chemicals offer advantages and benefits over others due to their physical properties. These advantages are primarily due to the humidity threshold at which they absorb moisture and liquify themselves, but may also involve some other physical or chemical property, such as temperature range, melting point, corrosiveness, toxicity, hazard rating or ease of handling. An important feature of the present invention is that the humidity level at which the deliquescent material will liquefy can be tailored by the proper selection of either a single deliquescent chemical or some proportionate combination of deliquescent materials. By choosing a mixture of deliquescent materials, a specific humidity level of activation can be selected. Therefore, the action of the device can be pre-determined to notify the user when varying levels or a range of humidity have been reached or exceeded.

A third key component of this invention is the color indicator. This may be of any form, shape, or material, and exists located behind the opaque deliquescent chemical, thus blocked from view by the opaque deliquescent material in its dry and solid form when observed from its only available viewing angle. Typically, this indicator material will be of a bright color, fluorescent orange or red, neon or dayglow, for example, and suitable to provide a brilliant and highly noticeable warning indication even where no prior prompting is given to look for such a warning. Any color can be specified to meet specific demands, but it would be particularly suitable to use colors that have international significance as to providing warnings, such as red or orange. One embodiment of the instant invention uses a heat-bonded high temperature vinyl in a color known as "Neon Tangerine Orange", part # NPTNG, manufactured by Apex Plastic Industries, Inc., New York. In this embodiment, the vinyl is bonded to an aluminum substrate, and then die punched to provide the necessary shape.

The color indicator will typically be made from a substrate that has a coating thereon. The coating may be any form of material suitable to provide a bright visual indication when seen through the viewing window after the device activates. Such material coating must be selected such that it is not soluble in water once it has been applied. Suitable materials include colored materials, such as vinyl (including vinyl laminates), paint (including epoxy paint), ink, dye, polymer, glass, acetate, polycarbonate, plastic, ceramic, or any other permanently colored or dyed composite, powder coated metals of various colors, or rigid substrates having a coating of these materials, attached through a permanent bonding process.

FIG. 1A describes, from a top view, the humidity indicator, which includes a clear sight glass (not shown) over the opaque deliquescent material 4, in this example housed within a hex head threaded enclosure 2, with the deliquescent chemical lithium chloride at the forefront of the inside of the sight glass, totally obscuring the color indicator 6 from view, since the color indicator 6 is located behind the opaque deliquescent material 4.

FIG. 1A depicts the device's resting, non-reactive, or non-indicating mode of operation. An observer will only be able to see the opaque deliquescent chemical 4 through the sight glass window. The opaque deliquescent material 4 will typically be a white color, but may also be a colored or dyed form of the deliquescent material thereby providing various initial, non-reactive, or resting colors other than white.

When water or moisture is present in the area of the lithium chloride or other deliquescent chemical, the opaque deliquescent material 4 absorbs the moisture into itself and dissolves. The rate of absorption is dependent upon the humidity level and the physical properties or characteristics of the deliquescent material, or combination of deliquescent materials, used. The rate at which the opaque deliquescent material 4 absorbs enough moisture to liquefy itself is dependent upon the above factors of humidity level and chemical properties, plus the added factors of weight of material used, density, and physical form as defined by the design of the device.

Under typical conditions, the change of the opaque deliquescent material 4 to its liquid phase will take place gradually, this being dependent upon the chemical properties of the deliquescent material, combination of materials used and humidity level. The estimated time frame to completely liquify may be between a few hours to a few days. The change to liquid will be instantaneous if the deliquescent material comes in direct contact with water.

Absorption of moisture and liquidization of the opaque deliquescent material 4 progresses from its outermost areas first, which are those areas in greatest contact with area humidity. The innermost areas, which are occluded from the moisture at first, will be the last to absorb enough moisture to liquify, because of the shielding action of the chemical itself, and by the function of the chemical in acting, to a certain degree, as a desiccant to pull moisture away or prevent moisture from reaching its innermost core. In this case, the opaque deliquescent material 4 liquefies or disappears slowly to reveal the color indicator 6, previously hidden behind it, in stages.

Figure 1B:
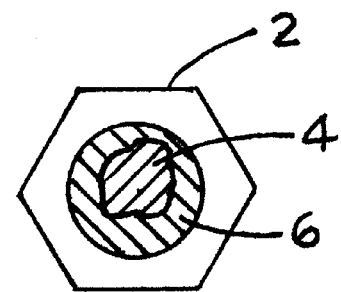
FIG. 1B illustrates, in top view, a partial dissolving of the opaque deliquescent material to allow show-through of the indicating layer.

FIG. 1B illustrates the invention, where some of the opaque deliquescent material 4 has liquefied and become transparent to show some of the color indicator 6 behind it, while some deliquescent material still remains.

Figure 1C:
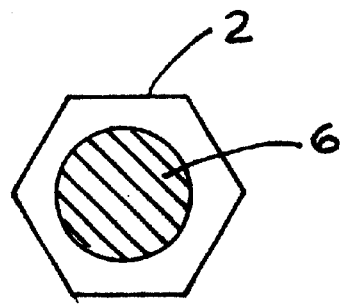
FIG. 1C shows, by top view, a complete show-through of the indicating layer after the opaque deliquescent material is completely dissolved, has become transparent, and the spring has pushed the indicating layer forward.

As seen in FIG. 1C, when the deliquescent material liquefies itself completely, the obscured color indicator material 6 becomes completely visible from the same viewing angle, and the color of that material will serve as the visual indication.

Figure 2:
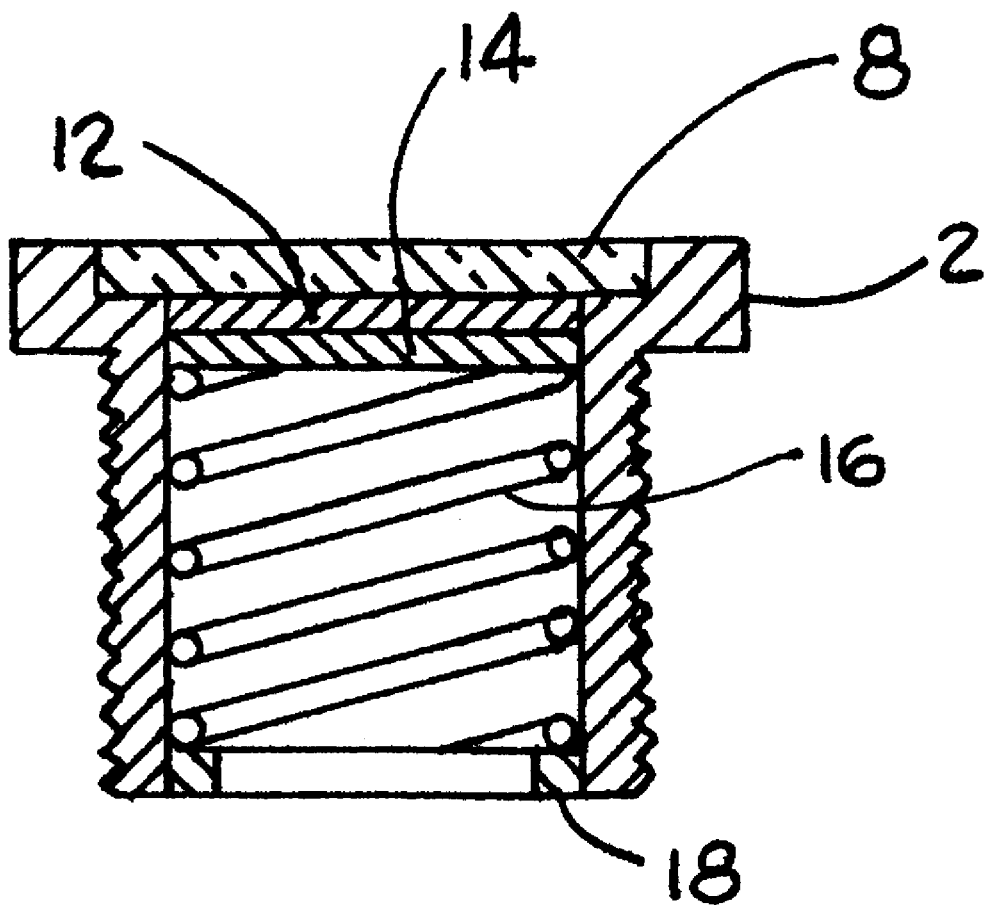
FIG. 2 is a cross-section of the device showing the placement of the individual layers and other components.

Referring briefly to FIG. 2, once the chemical transformation of the deliquescent material from solid to liquid form is fully completed, no evidence of the deliquescent material layer 12 remains, and the color indicator layer 14 is at its most forward position resting against the inside surface of the sight glass or viewing window 8. FIG. 1C depicts the invention in this final form following completion of the transformation from solid to liquid.

From FIG. 2, it can be seen that a device, such as a compression spring 16, or some other means of applying a force, provides slight pressure to the rear side of the color indicator layer 14 and moves the indicator forward to rest immediately next to the viewing window 8, as the deliquescent material layer 12 liquefies and is pressed outward from the space between the viewing window and the color indicator. This spring 16 then ensures the greatest view of the color indicator layer 14 through the viewing window 8. The opposite side of the spring mechanism rests against some form of fixed spring stop 18 in order to provide a forward moving force to drive the color indicator layer 14 toward the viewing window 8. One end of the device is open to the environment to be monitored to allow moisture to enter the monitoring device.

In one embodiment, as shown in FIG. 2, the present invention consists of a clear sight glass viewing window 8 housed in an enclosure 2 of metal or plastic, having a volume of opaque deliquescent material in the form of a layer 12 fully covering the viewing area, said deliquescent material being of sufficient density and thickness to totally obscure sight of the colored indicator layer 14 behind it. The sight glass viewing window 8 may be formed from a glass, vinyl, plastic, acetate, or any transparent or translucent material capable of providing a clear view, adequate to see the color indicator layer 14 once the deliquescent material layer 12 has become transparent or has otherwise disappeared.

Behind the opaque deliquescent material layer 12 rests a material providing a color indication on its forward surface. For purposes of stability, that color might be adhered to some heavier substrate, though this is not necessary. Behind the color indicator layer 14, a light coil spring 16 or other resistive force provides a constant push on the colored indicator layer 14, driving it forward against the deliquescent material layer 12. As the deliquescent material layer 12 liquefies, the spring 16 pushes the color indicator layer 14 to the most forward position and squeezes any liquid to the rear around and past the edges of the color indicator layer 14. The color indicator layer 14 then rests at the very front of the glass viewing window 8 area and serves as a visual indication that a certain degree of humidity has been reached or exceeded. The level of humidity adequate to cause the deliquescent material layer 12 to liquify, results in an indication, which is designed into the invention, based upon the proper selection of deliquescent material or combination of deliquescent materials.

The invention may consist of various forms depending upon the specific application. It may be housed within a threaded sight glass enclosure 2 for insertion into a housing or closed environment. It may also be enclosed within a hollow cylinder having one forward end clear for viewing, and even may have both ends incorporating a clear viewing pane, thus existing as a stand-alone humidity indicator. A cylinder or housing having dual viewing areas would easily allow indication of different humidity ranges within the same device.

Figure 3:
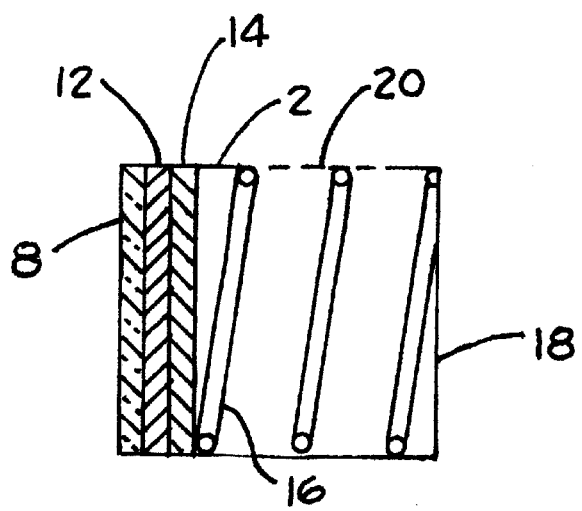
FIG. 3 is a cross-section of an embodiment of the present invention that may be used as a stand-alone device.

FIG. 3 is an embodiment of the present invention that may be used as a stand-alone device, such as to be included in packaging to determine whether it has been subjected to water. The enclosure 2 is permeable to water, or has a permeable surface section 20 or membrane that is permeable to water. Visibility is accomplished through a viewing window 8. Immediately next to the viewing window is a deliquescent material layer 12 and on the other side of that is the color indicator layer 14. Pressing against the indicator layer is a spring 16. The spring 16, at its other extremity, presses against the end of the enclosure housing, which serves as a spring stop 18. Once a level of moisture has entered this device and liquefied the deliquescent material layer 12, the spring will force the color indicator layer 14 forward against the viewing window 8, giving a permanent indication that a certain level of moisture has been present.

Figure 4:
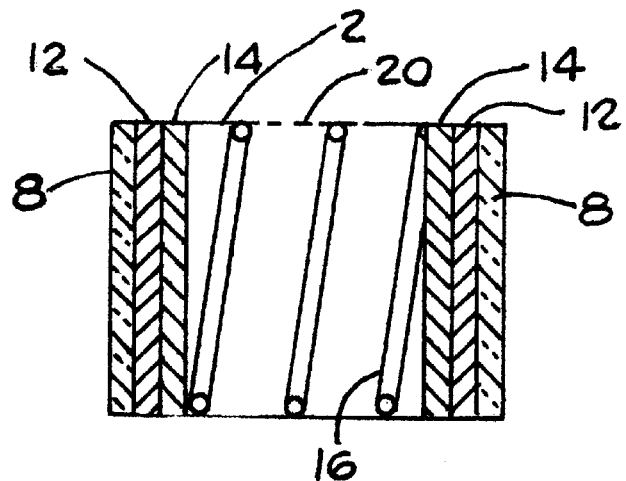
FIG. 4 shows, by cross-section, the present invention as a stand-alone device with indicators at both ends.

FIG. 4 is a double-ended version of the device depicted in FIG. 3. In FIG. 4, there are viewing windows 8 at both ends of the device. In each case, there is a deliquescent material layer 12 adjacent to the viewing window 8. On the other side of the deliquescent material layer 12, there is a color indicator layer 14 for each end of the device. The spring 16 pushes against the color indicator layers 14 at both ends of the device. The deliquescent materials may be selected to have different rates of moisture pickup, thus providing indication of two different levels of moisture having been reached. The color indicator layers 14 would be selected to have different colors to provide visual response of the two different layers of moisture. As in FIG. 3, the enclosure 2 of FIG. 4 is permeable to water or has a permeable surface section 20 incorporated therein.

Figure 5A:
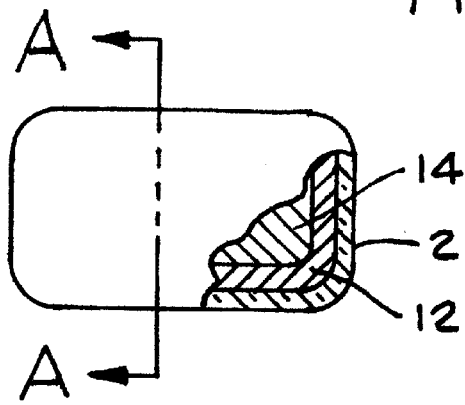
FIG. 5A depicts the present invention in the form of a capsule.
Figure 5B:
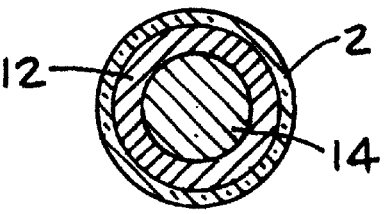
FIG. 5B illustrates a cross-section taken at A—A of FIG. 5A.

The present invention may also be made in the form of a capsule as is depicted by FIG. 5A and in cross-section FIG. 5B, wherein the opaque deliquescent material layer 12 is coated on the inside of the capsule with the color indicator material 14 in the interior. The capsule enclosure 2 is permeable to water allowing the deliquescent material layer 12 to liquify and become transparent. Thus, the color indicator layer 14 would be visible once the deliquescent material layer 12 has liquefied.

The present invention may also be used as a component of a corrosion monitor, such as that described in U.S. Pat. No. 6,131,433 to the author of the present invention (Duncan), which is incorporated herein by reference. Utilizing the present invention as part of a corrosion monitor has several advantages. One is low cost; another is simplicity. Additionally, a monitor made with the present invention will provide an immediate indication when the wall of a water containment system has corroded away.

The present invention may be included as part of a monitor that may be easily removed from service and replaced with another unit quickly.

A corrosion monitor made using the present invention as an indicator is extremely economical in comparison to all other corrosion monitoring devices and instrumentation, thereby extending corrosion monitoring protection further throughout any testing location or service application.

There is no form of maintenance to the present invention and the product has an indefinite operating life in an environment having a humidity level of less than the reaction or triggering level of the device. An important feature of the monitor of the present invention is the ability to be used in different areas. Unlike prior art, which may require a fixed location, the humidity monitor of the present invention can be utilized anywhere, and requires no electrical hookup or further testing or analysis.

Conclusions, Ramifications, and Scope

The present invention serves as an indicator of the presence of humidity. It can be made simply from inexpensive materials. It is flexible in application, error-free (such as avoiding false negative responses), persistent, and unequivocal in its indication of humidity.

The humidity indicator features a brilliant visual indication not dependent upon a chemical color change, a color change to any color, tone or intensity desired, and simple manufacture using paint, epoxy, or any other material of color.

It will not wash out or dissolve due to saturation in the liquid environment, will remain to provide indication of a problem condition without the fear that noticeability of the indication will be lost if not immediately observed.

It can be used in any location and thus, along with its low cost, it will provide a benefit by allowing the monitoring of a greater number of areas of concern.

When incorporated as part of a corrosion monitoring system for any pipe, tank, pressure vessel, reaction vessel or other water containment or transmission system, it will indicate a breakthrough of the containment vessel surface.

This humidity monitor can be made as a disposable, self contained, stand alone device not requiring any further evaluation, energy, information processing, handling, maintenance or testing in order to produce an indication of the presence of humidity.

While the invention has been described with reference to specific details and examples of the preferred embodiments, it will be understood by those skilled in the art that various changes may be made and equivalents may be substituted for elements thereof, without departing from the scope of the invention. In addition, many modifications may be made to adapt a particular situation or material to the teachings of this invention without departing from the essential scope thereof. Therefore, it is intended that the invention not be limited to the particular embodiments disclosed as the best mode contemplated for carrying out this invention, but that the invention will include all embodiments falling within the scope of the claims below and their legal equivalents.

I claim:

1. A device for monitoring humidity, comprising:
   a) a first layer comprising a visual indicator;
   b) a second layer, covering and obscuring said first layer, said second layer comprising a deliquescent material, wherein said deliquescent material picks up moisture and dissolves itself in the moisture, becoming transparent and exposing said first layer;
   c) viewing means disposed on the opposite side of said second layer from said first layer;
   d) urging means for moving said visual indicator, wherein said urging means is activated by deliquescing of said deliquescent material;
   e) an enclosure containing said first and second layers, said spring means, and said viewing means; and
   f) an entrance to said enclosure,
      whereby moisture may enter and react with said deliquescent material.

2. The humidity monitoring device of claim 1, wherein said urging means comprises spring means, and wherein one end of said spring means is placed behind and against said first visual indicator layer and the other end of said spring means is fixed against a stop, such that said spring means causes pressure to be exerted against said first visual indicator layer, pushing it towards said viewing means, such that said first visual indicator layer travels in the direction of said viewing means once said deliquescent material layer has dissolved.

3. The humidity monitoring device of claim 2, wherein said deliquescent material layer liquefies and is excluded from its original location by the force of said spring means.

4. The humidity monitoring device of claim 1, further characterized by selecting a mixture of deliquescent materials each having a different level of moisture that leads to deliquescence, whereby said mixture liquefies at a level of moisture characteristic of the mixture and not the individual components thereof.

5. The humidity monitoring device of claim 1, wherein said enclosure, said viewing means and said entrance are made of the same material, thus forming the containment surface of a capsule.

6. The humidity monitoring device of claim 1, wherein said viewing means is formed from a transparent material.

7. The humidity monitoring device of claim 1, wherein said viewing means is made from a translucent material.

8. The humidity monitoring device of claim 1, wherein said viewing means is constructed from a material selected from the group consisting of glass and plastic.

9. The humidity monitoring device of claim 8, wherein said plastic is selected from a group consisting of polycarbonate, vinyl and acetate.

10. The humidity monitoring device of claim 1, wherein said enclosure is made of a material selected from the group consisting of metal and plastic.

11. The humidity monitoring device of claim 1, wherein said deliquescent material is selected from the group consisting of metal chlorides, metal fluorides, metal hydroxides, metal carbonates, and metal nitrates.

12. The humidity monitoring device of claim 11, wherein said metal chlorides are selected from a grout consisting of all alkali metal chlorides.

13. The humidity monitoring device of claim 11, wherein said metal chlorides are selected from a group consisting of all alkaline earth metal chlorides.

14. The humidity monitoring device of claim 11, wherein said metal chlorides are selected from a group consisting of all transition metal chlorides.

15. The humidity monitoring device of claim 1, wherein said deliquescent material is selected from the group consisting of lithium chloride, sodium hydroxide, potassium fluoride, potassium carbonate, potassium nitrate, magnesium chloride, stannous chloride, strontium chloride, aluminum chloride, calcium chloride, zinc chloride, calcium nitrate, sodium nitrate, ammonium chloride and ammonium nitrate.

16. The humidity monitoring device of claim 1, wherein said visual indicator comprises a substrate and a coating thereon.

17. The humidity monitoring device of claim 16 wherein said coating comprises a colored material selected from the group consisting of vinyl, vinyl laminates, paint, epoxy paint, inks, dyes, polymers, glass, acetates, polycarbonates, plastics, ceramics, composites, and powder coats.

18. The humidity monitoring device of claim 17, wherein said substrate is rigid and wherein said colored material is attached to said rigid substrate through a permanent bonding process.

19. The humidity monitoring device of claim 17, wherein the color of said colored material is selected from the group consisting of red, orange, yellow and pink.

20. The humidity indicating device of claim 1, wherein said enclosure contains a section permeable to water, thus forming said entrance.

21. The humidity indicating device of claim 1, said enclosure comprising a water permeable material.

22. A self-contained, disposable corrosion monitor for a fluid containing system comprising:
   a plug insertable into a fluid containing system, said plug indicating a preselected amount of loss of metal on an inner wall of said fluid containing system due to corrosive action of said fluid on said inner wall of said fluid containing system, said plug including
   a) a solid monitoring wall of a predetermined metal having a thickness equal to said preselected amount of loss and one surface exposed to said fluid when said plug is inserted into said fluid containing system at the same level as said inner wall of said fluid containing system,
   b) an enclosed cavity associated with the other surface of said solid monitoring wall, and
   c) a substance disposed within said enclosed cavity reacting with said fluid penetrating said solid monitoring wall to indicate when said fluid has penetrated said solid monitoring wall and, hence, that said preselected amount of loss of said metal on said inner wall of said fluid containing system has occurred; wherein said substance disposed within said enclosed cavity comprises the humidity monitoring device of claim 1, whereby said corrosion monitor is suitable for water-based environments.

23. A method for detecting humidity, comprising the steps of:
  a) providing a color indicator;
  b) covering said indicator with a layer of deliquescent material;
  c) providing spring means for moving said indicator;
  d) placing said indicator and said spring means in an enclosure;
  e) providing a means for viewing said indicator from the deliquescent material side; and
  f) providing an entry means for water to access the deliquescent material.

24. A device for monitoring humidity, comprising:
  a) a first layer having one side coated with a visual indicator material and the other side uncoated;
  b) a second layer comprising deliquescent material, covering and obscuring said coated side of said first layer, wherein said deliquescent material picks up moisture and dissolves itself in the moisture, becoming transparent and exposing said coated side of said first layer;
  c) a third layer having one side coated with a visual indicator material differing in color from that of said first layer, and the other side uncoated;
  d) a fourth layer comprising a different deliquescent material from that in said second layer, said fourth layer covering and obscuring said third layer, wherein said deliquescent material picks up moisture and dissolves itself in said moisture, becoming transparent and exposing said coated side of said third layer;
  e) a spring in contact at one end with said uncoated side of said first layer visual indicator and in contact at the other end with said uncoated side of said third layer visual indicator;
  f) a viewing means disposed on the opposite side of each deliquescent material layer from said first and third visual indicator layers;
  g) an enclosure containing said first, second, third and fourth layers, said spring and said viewing means; and
  h) an entrance to the enclosure, whereby when moisture enters and reacts with the deliquescent material, which liquefies and dissolves, said first and third visual indicator layers are propelled forward against said viewing means by the force of the spring.

* * * * *